Figure 1:
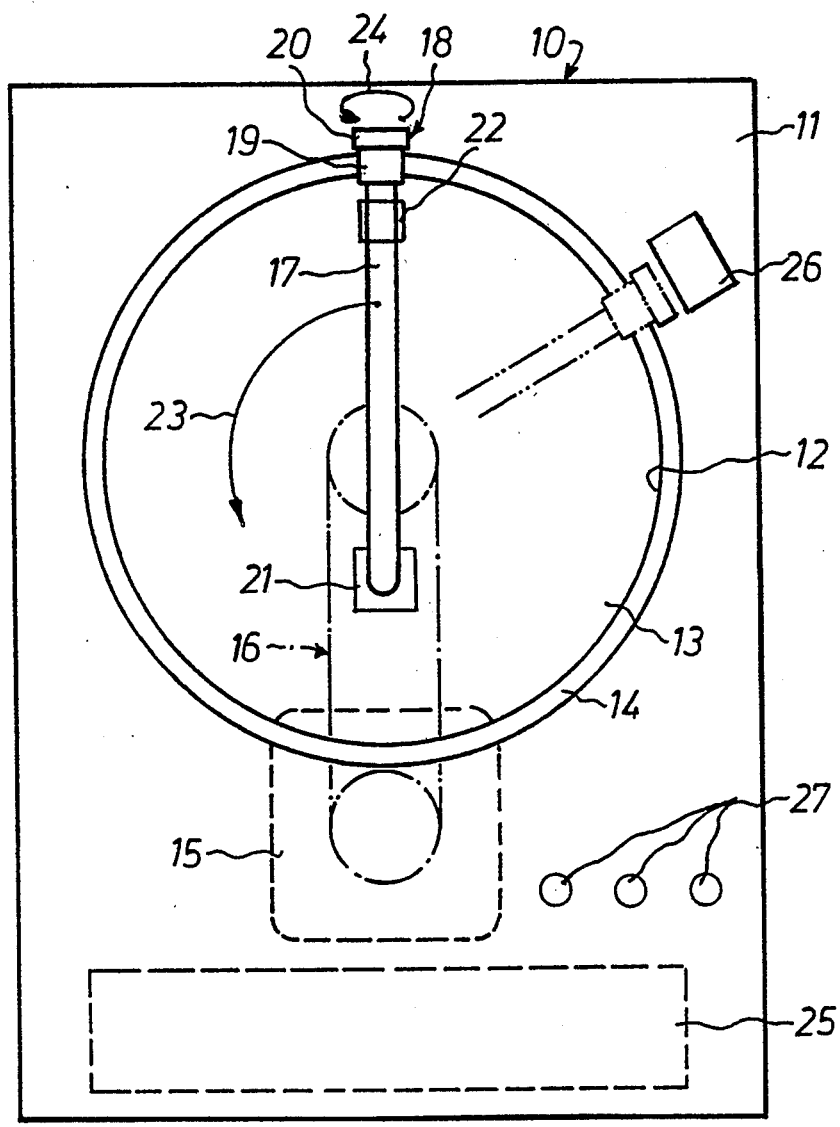

United States Patent [19]

Nilsson et al.

[11] Patent Number: 5,367,157
[45] Date of Patent: Nov. 22, 1994

[54] DEVICE FOR RAPIDLY PERFORMING A SEDIMENTATION-RATE TEST

[75] Inventors: Sven-Erik Nilsson; Jan E. Lilja, both of Helsingborg, Sweden

[73] Assignee: Hemocue AB, Angelholm, Sweden

[21] Appl. No.: 66,174

[22] PCT Filed: Nov. 27, 1991

[86] PCT No.: PCT/SE91/00806
§ 371 Date: Aug. 2, 1993
§ 102(e) Date: Aug. 2, 1993

[87] PCT Pub. No.: WO92/09879
PCT Pub. Date: Jun. 11, 1992

[30] Foreign Application Priority Data

Nov. 29, 1990 [SE] Sweden .................... 9003799

[51] Int. Cl.$^5$ ............................. G01D 5/34
[52] U.S. Cl. ................. 250/231.13; 73/61.66
[58] Field of Search .............. 250/231.13; 356/39, 356/427; 73/61.65, 61.66, 61.71; 422/73, 72; 436/70; 494/27, 37, 10

[56] References Cited

U.S. PATENT DOCUMENTS

| | | | |
|---|---|---|---|
| 3,199,775 | 9/1961 | Drucker | 233/25 |
| 3,614,434 | 10/1971 | Horwitz et al. | 250/71.5 |
| 5,133,208 | 7/1992 | Ricci | 73/61.66 |

FOREIGN PATENT DOCUMENTS 2153072A 8/1985 United Kingdom.

Primary Examiner—David C. Nelms
Assistant Examiner—Steven L. Nichols
Attorney, Agent, or Firm—Burns, Doane, Swecker & Mathis

[57] ABSTRACT

A device for rapidly performing a sedimentation-rate test is described. A tube (17) containing a given amount of blood specimen is placed in a holder (13, 21, 22) which rotates (23) the tube (17) a predetermined number of revolutions at a given speed about an axis perpendicular to the longitudinal axis of the tube while rotating (24) the tube about its longitudinal axis, to then stop the tube for a given period of time about 60° from the vertical, and to finally turn the tube (17) to the vertical position at a speed which is but a fraction of the first-mentioned speed also while turning the tube about the longitudinal axis. Means (26) are arranged to monitor the rotational movements of the tube, preferably by means of markings on a plug (18) closing the tube end.

11 Claims, 2 Drawing Sheets

DEVICE FOR RAPIDLY PERFORMING A SEDIMENTATION-RATE TEST

The present invention relates to a device for rapidly performing a sedimentation-rate test, comprising an elongate lid-equipped vessel for receiving a given amount of blood, and a frame with a holder for said vessel which, when disposed in the frame, is rotatable in the vertical plane about an axis perpendicular to its longitudinal axis, and rotatable about its longitudinal axis.

The sedimentation-rate test is a blood test commonly used in medical check-ups. It is a non-specific test, but gives, when combined with Other tests, an idea of e.g. on-going inflammatory processes.

Today, the sedimentation-rate test is standardized by national and international organizations, such as the NCCLS, the ICSH and the WHO. In most cases, it is performed by letting a tube (vessel), which has a length of about 250 mm and an inner diameter of about 2.54 mm, be filled with a mixture of citrate and blood at room temperature to a height of 200 mm, and placing the tube in the vertical position for 60 min. Then, the sedimentation-rate is read as the decrease in height (nun) of the red blood column compared with the original height. The overall testing time is about 70–75 min, including the cooling of the blood to room temperature. The blood used in the sedimentation-rate test may be either venous or capillary blood.

Stein W: 'Blutsenkungen in 10 Mlnuten-Verfahren' Med. Mschr 1949, 3, pp 919–921 describes a quick sedimentation rate test of common type used. In this method, the sedimentation tube is placed at an angle of 60° to the vertical, and the sedimentation-rate value in mm/h can be read after 10 min. However, this method requires reading experience, and is not widely used. Norwegian Patent 153,508 discloses a modified version of the quick sedimentation rate test according to Stein. In the Norwegian method, which is used for simplifying the reading of a tilted sedimentation tube, the tube is, while turned a certain number of revolutions, erected to the vertical position where a conventional reading is performed.

When testing venous blood of which a few millimeters are available, a specimen is taken by means of a syringe, often filled with a suitable quantity of citrate, or a vacuum tube filled beforehand with citrate. The vacuum tube is highly advantageous in terms of hygiene, since the blood and the citrate thus are mixed in a tube where the proportion of blood to citrate is ensured by the vacuum present in the tube when the blood specimen is taken. In a standardized sedimentation tube design, the tube (vessel) is then filled with the solution of titrate and blood, as described earlier. In cases where the sedimentation rate is read directly from a vacuum tube with an inner diameter exceeding 3 mm, the vacuum tube is placed in the vertical position, and after the solution has been brought to room temperature with intense mixing in the vertical position, the sedimentation rate is read after 60 min in the manner described. When the sedimentation rate is read directly from short vacuum tubes in which the height of the blood column is less than 200 mm, a conversion scale is employed to give a sedimentation-rate numerical value equivalent to that obtained by the standardized method. In an article by B. HJalmarsson, published in Laboratoriet No. 6/85, a vacuum-tube system for sedimentation-rate tests is described, which employs a tube with an inner diameter of 9 mm. It appears from this article that the analysis takes at least 70 min when a vacuum tube is used, including the time required for mixing and bringing the solution to room temperature.

If capillary blood, e.g. taken from the fingertips, is used, only small quantities of blood are available. A special method is required when the capillary blood is diluted with a quantity of citrate corresponding to a dilution ratio of blood to citrate of 1/41, and the citrated blood is agitated and drawn up in a tube with a total volume which usually is less than 150 $\mu$l. The inner diameter of a suitable tube then is in the order of 1 mm.

One object of the present invention is to provide a device for implementing the method of Norwegian Patent 153,508 and, in addition, to reduce the time required for the analysis by making provisions for e mixing operation before the analysis. Another object of the invention is to provide a vessel, preferably a vacuum tube, which is to be used in the device to enable hygienic handling and minimize the risk of the device being contaminated. A further object of the invention is to provide means for verifying that the tube has performed certain movements.

The objects of the invention are achieved by the device set forth in the appended claims.

Figure 2:
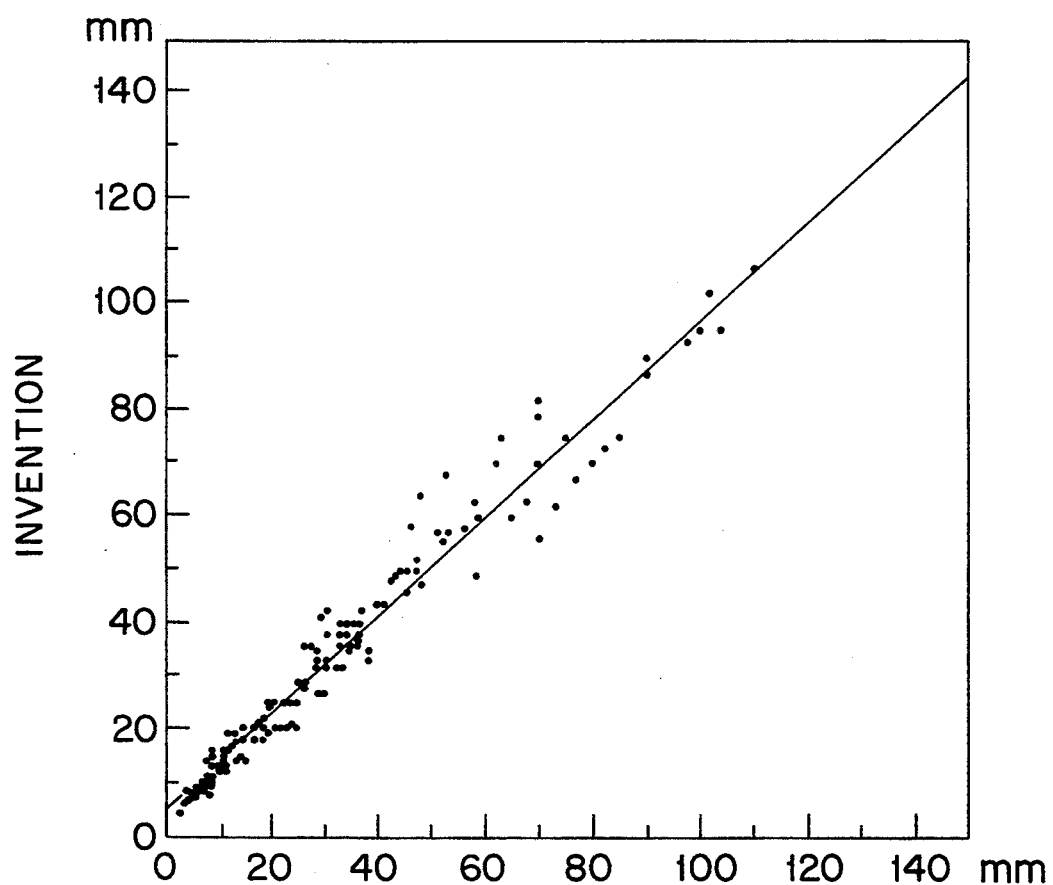

The invention will be described in more detail below with reference to the accompanying drawings, in which FIG. 1 schematically illustrates an embodiment, and FIG. 2 is a graphic comparison between the device of the invention and a prior-art device. Specimen values are shown as dots and a solid regression line is shown wherein Y=a+bx, a=5.00, b=0.92, r=0.983, and n=153.

FIG. 1 is a front view of a device for rapidly performing a sedimentation-rate test, which consists of a frame in the form of a closed housing 10, preferably of plastic. The housing 10, which is intended to be placed on a table, has a vertical front 11 which is formed with a circular through opening 12 in which a circular disc 13 is rotatably mounted. Around the opening is provided an annular ridge or flange 14 which may be integrally formed with the front 11 of the housing 10 or consist of a ring non-rotatably fixed in the opening. The disc 13 is rotated in the opening 12 by a motor 15 (indicated by broken lines) through a transmission (indicated by dashdot lines). The motor 15, which preferably is a step motor, can be accurately controlled as to the speed of rotation.

To perform the sedimentation-rate test, use is made of a vessel for receiving the blood specimen. The vessel preferably is a tube 17 whose ends are closed, one permanently and the other by a plug generally designated 18. The plug 18 is made of rubber or plastic, or a combination of the two, and has, as shown in FIG. 1, a lower cylindrical part 19 sealingly applied to the tube wall, and an upper cylindrical part 20 having a slightly larger diameter than the lower part 19. The plug is so designed that a cannula can be run therethrough from the end surface to supply the blood specimen, and when the cannula is then withdrawn, the supply opening closes automatically. A tube of this type suitably has such a length that the height of the blood column can be at least 100 mm, and is delivered filled with titrate solution. Although different sorts of tubes can be used, a vacuum tube is especially suitable. A vacuum tube is a tube from which the air has been evacuated before the insertion of the plug, to give a certain negative pressure in the tube. In the taking of specimens, a vacuum tube is automatically filled with a given quantity of blood when the negative pressure in the tube returns to normal, i.e. to the ambient pressure.

To perform the quick sedimentation-rate test, the tube is placed on the end surface of the disc 13 facing away from the housing 10, with the aid of a bearing means 21, in which the end of the tube 17 remote from the plug 18 is rotatably mounted, and an additional bearing means 22 through which the tube 17 can be passed and which also permits rotation of the tube 17. The bearing means 21 is arranged at some distance from the center of the disc 13, and the bearing means 22 is, as can be seen in FIG. 1, aligned with the bearing means 21 and located on the same diameter; The distance between the center of the disc 13 and the bearing means 21 is such that the cylindrical part 19 of the plug 18 for the tube 17 will be pressed against the flange 14 with a predetermined friction when the tube is placed in the two bearing means. When the disc 13 is rotated by the motor 15 and the transmission 16, and the tube 17 rotatably mounted on the disc by the bearing means 21 and 22 is rotated about an axis perpendicular to the longitudinal axis of the tube, the tube 17 will also rotate about its longitudinal axis, as indicated by an arrow 24, owing to the engagement between the flange 14 and the plug 18. Thus, the tube 17 is rotated about the axis perpendicular to the longitudinal axis of the tube in the vertical plane by means of the motor 15 and the transmission 16, as indicated by an arrow 23, and at the same time about its longitudinal axis, as indicated by the arrow 24. When performing the sedimentation-rate test, it is essential that these rotational movements are as accurate as possible, for which reason a processor 25 is provided in the housing 10. Further, means are arranged for monitoring the rotational movements. These means may be of electric or magnetic type, but preferably consist of an optical transducer 26 arranged in a projecting part of the front 11 of the housing 10, opposite to the path of movement of the rotating tube 17, as illustrated in FIG. 1. When the plug passes, the optical transducer 26 scans for a suitable marking on the end surface of the plug portion 20 facing the transducer. However, this marking need not be provided on the end surface, but may be placed elsewhere on the plug 18 or on the tube 17 itself, in which case the transducer 26 naturally has to be arranged otherwise than in FIG. 1. As indicated at 27, signal lamps and switches may also be provided on the housing 10. The motor 15, the transducer 26 and the signal lamps and switches at 27 are, of course, connected to the processor 25 by lines not shown in FIG. 1.

When performing a sedimentation-rate test, the blood specimen is first injected into the tube 17 by means of a suitable cannula, or the tube is automatically filled if being a vacuum tube. The tube 17, already containing a citrate solution, is then placed in the bearing means 22 and 21 with the plug portion 19 contacting the flange 14. The motor 15 is then started by means of a switch, and the tube 17 is rotated a predetermined number of revolutions for a given time in the vertical plane in the direction indicated by the arrow 23. Thereafter, the motor 15 is stopped in a position in which the tube 17 is about 60° from the vertical, as indicated by double-dotted-dash lines. The tube 17 is maintained in this position for a given period of time, whereupon the motor 15 is again started and moves the tube from the 60° position to an erect position, i.e. along the vertical. The tube 17 is moved to the vertical position at a speed which is but a fraction of the first-mentioned speed. In practice, a tube 17 with an inner diameter of 6 mm may first be rotated through 8 5/6 revolutions in the direction indicated by the arrow 23 and through 106 revolutions in the direction indicated by the arrow 24 in the course of about 3 min, to be subsequently maintained stationary in the position about 60° from the vertical for about 9 min, and finally be turned from the 60° position to the vertical position in the course of 10 min, the tube 17 rotating two revolutions about its longitudinal axis.

When the tube 17 after these movements has been placed along the vertical, the sedimentation-rate is measured, which may be carried out by a scale fixedly or adjustably arranged on the disc 13 or by a loose scale.

The device described above and illustrated in FIG. 1 is very easy to handle and advantageous also from the point of view of hygiene. However, it goes without saying that the device may be designed in many other ways, provided that the tube 17 moves about and perpendicular to its longitudinal axis for given periods of time, as stated.

The device according to the invention was used in a study aiming at comparing the quick sedimentation-rate test of the invention with a vacuum tube commercially available for this purpose, Seditainer ®, Becton Dickison, Rutherford, N.J., USA. The study bore upon 153 specimens. One blood specimen was taken with Seditainer ® and one was taken with the tube according to the invention. The results are shown in FIG. 2. As is apparent, a correlation factor of 0.98 and a regression line $y = 0.92 \times + 5$ were obtained. Thus, the device according to the invention is well up to the standard of a commercially available method.

We claim:

1. A device for rapidly performing a sedimentation-rate test, comprising an elongate vessel, which is equipped with a lid and has a longitudinal axis, said vessel being adapted to receive a given amount of blood, and a frame with a holder for said vessel which, when disposed in the frame, is rotatable in a vertical plane about a horizontal axis perpendicular to the longitudinal axis, and rotatable about the longitudinal axis, wherein said holder is adapted to rotate the vessel a predetermined number of revolutions at a first speed about the horizontal axis, while simultaneously turning the vessel about the longitudinal axis, and then stop the vessel, for a given period of time, in an angled position in which the longitudinal axis forms a predetermined angle with a vertical position, to subsequently turn the vessel about the horizontal axis from said angled position to said vertical position and a sedimentation-rate-measuring site at a second speed which is but a fraction of said first speed also while turning the vessel about the longitudinal axis.

2. A device as claimed in claim 1, further comprising means for monitoring rotational movements of the vessel by means of markings provided on the vessel.

3. A device as claimed in claim 2, wherein said means for monitoring rotational movements of the vessel comprises electric means.

4. A device as claimed in claim 2, wherein said means for monitoring rotational movements of the vessel comprises magnetic means.

5. A device as claimed in claim 2, wherein said means for monitoring rotational movements of the vessel comprises optical means.

6. A device as claimed in claim 2, wherein said markings are provided on the lid of the vessel.

7. A device as claimed in claim 2, wherein said means for monitoring rotational movements of the vessel is an optical transducer arranged diametrically outside a path of movement of the vessel and arranged to sense a marking on the end surface of the lid.

8. A device as claimed in claims 1, wherein said vessel is a tube having an open end, wherein said lid is a pierceable, self-sealing plug, which closes said open end of the tub and which presents a cylindrical surface, and wherein said holder of the frame is surrounded by a circular ring, said tube being so positionable in the holder that said cylindrical surface of the plug is in engagement against the ring, whereby the tube, while rotating about the horizontal axis, is rotated about the longitudinal axis owing to said engagement between the ring and the cylindrical surface of the plug.

9. A device as claimed in claim 8, wherein said holder comprises a circular, flat disc which, on a side facing outwards and away from the frame, has a first bearing means for an end of the tube opposite to said open end closed by the plug, said first bearing means being arranged on a diameter of the disc at a distance from a center of the disc, and second bearing means being arranged on said diameter close to a periphery of the disc.

10. A device as claimed in claim 1, further comprising a step motor for rotating said holder of the frame, and a processor for controlling said step motor and being connected to said monitoring means.

11. A device as claimed in claim 1, wherein said vessel is a tube having an inner diameter of about 6 mm, and wherein the holder is adapted to rotate the tube through 8 5/6 revolutions in the course of about 3 min. about the horizontal axis while rotating the tube through 106 revolutions about the longitudinal axis, to keep the tube stationary in said first position about 60° from said vertical position for about 9 min., and to finally turn the tube through a remaining angle of about 60° to said vertical position and through 2 revolutions about the longitudinal axis in the course of about 10 min.

* * * * *